United States Patent [19]

Collins et al.

[11] 4,133,959

[45] Jan. 2, 1979

[54] ARYLOXYALKYL DIKETONES

[75] Inventors: Joseph C. Collins, East Greenbush; Guy D. Diana, Stephentown, both of N.Y.

[73] Assignee: Sterling Drug Inc., New York, N.Y.

[21] Appl. No.: 725,160

[22] Filed: Sep. 21, 1976

Related U.S. Application Data

[63] Continuation-in-part of Ser. No. 576,311, May 12, 1975, Pat. No. 4,031,246, which is a continuation-in-part of Ser. No. 381,406, Jul. 23, 1973, Pat. No. 3,933,837.

[51] Int. Cl.$^2$ .............................................. C07C 69/76
[52] U.S. Cl. ..................... 560/53; 424/308; 562/463
[58] Field of Search ...................... 260/473 R, 521 B; 560/53

[56] References Cited

U.S. PATENT DOCUMENTS

| | | | |
|---|---|---|---|
| 3,769,320 | 10/1973 | Chodnekar et al. | 260/473 R |
| 3,833,642 | 9/1974 | Chodnekar et al. | 260/473 R |
| 3,868,406 | 2/1975 | Siddall | 260/473 R |
| 3,879,429 | 4/1975 | Chodnekar et al. | 260/473 R |

Primary Examiner—Paul J. Killos
Attorney, Agent, or Firm—Thomas L. Johnson; B. Woodrow Wyatt

[57] ABSTRACT

Aryloxyalkyl diketones, useful as anti-viral agents, are prepared from an aryloxyalkyl halide and an alkali metal enolate salt of a diketone or keto-ester, or from a haloalkyl-diketone and an alkali metal salt of a phenol.

16 Claims, No Drawings

ARYLOXYALKYL DIKETONES

This application is a continuation-in-part of copending application Ser. No. 576,311, filed May 12, 1975, now U.S. Pat. No. 4,031,246, which is in turn a continuation-in-part of application Ser. No. 381,406, filed July 23, 1973, now U.S. Pat. No. 3,933,837.

BACKGROUND OF THE INVENTION (a) Field of the Invention

This invention relates to aryloxyalkyl diketone and keto-esters, to the preparation thereof and to compositions and methods for the use thereof as anti-viral agents.

(b) Description of the Prior Art

Chodneker et al. U.S. Pat. No. 3,686,222 discloses ethers of the formula R-O-Ar wherein Ar is methylenedioxyphenyl and R is an aliphatic hydrocarbon radical or an epoxide derivative thereof, useful as pesticides having juvenile hormone activity.

Erickson U.S. Pat. No. 3,787,443 discloses ethers of the formula R-O-Ar wherein Ar is methylenedioxyphenyl or other substituted phenyl groups, and R is an aliphatic hydrocarbon radical or an epoxide or episulfide derivative thereof, useful as pesticides having juvenile hormone activity.

Collins U.S. Pat. No. 3,829,475 discloses diketones and keto-esters of the formula RR'CH—Alk—Ar wherein R is acyl, R' is acyl or carboalkoxy, Alk is an alkylene bridge and Ar is phenyl or substituted phenyl, useful as pesticidal and anti-viral agents; no aryl ethers are disclosed.

SUMMARY OF THE INVENTION

In a composition of matter aspect, the invention relates to compounds of the formula RR'CH—Alk—O—Ar wherein R is alkanoyl or carbalkoxy, R' is alkanoyl, Alk is alkylene and Ar is phenyl or substituted phenyl, useful as anti-viral agents.

In further composition of matter aspects, the invention relates to intermediates of the formula RR'CH—Alk—X where Alk is alkylene and X is Br or I; and intermediates of the formula 2—Cl—4—CH$_3$O—C$_6$H$_3$—O—Alk'—Cl where Alk' is alkylene interrupted by an oxygen atom.

In a further composition of matter aspect, the invention relates to a composition for combatting viruses which comprises an antivirally effective amount of a compound of the formula RR'CH—Alk—OAr in admixture with a suitable carrier or diluent.

In a process aspect, the invention relates to a process for obtaining the compounds of the invention by treating a compound of the formula X—Alk—O—Ar, where X is bromine or iodine, with a compound of the formula R'CH$^-$M$^+$ where M$^+$ is an alkali metal cation; or, conversely, reacting a compound of the formula RR'CH—Alk—X with a compound of the formula ArO$^-$M$^+$.

In a further process aspect, the invention relates to a method for combatting viruses which comprises contacting the locus of said viruses with an anti-virally effective amount of a compound of the formula RR'CH—Alk—OAr in admixture with a suitable carrier or diluent.

DETAILED DESCRIPTION INCLUSIVE OF PREFERRED EMBODIMENTS

The compounds of the invention are of the structural formula

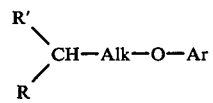

I wherein:

Alk is alkylene of 3 to 10 carbon atoms optionally interrupted by an oxygen atom separated by at least two carbon atoms from the terminal bonds of Alk;

R is alkanoyl of 2 to 6 carbon atoms;

R' is alkanoyl of 2 to 6 carbon atoms or carboalkoxy of 2 to 6 carbon atoms;

and Ar is phenyl or phenyl substituted by one to three substituents selected from the group consisting of alkyl of 1 to 4 carbon atoms, alkoxy of 1 to 4 carbon atoms, alkylthio of 1 to 4 carbon atoms, alkoxyalkoxy of 3 to 6 carbon atoms, hydroxyalkoxy of 2 to 4 carbon atoms, halogen, cyano, nitro, acetyl, sulfo, aminosulfonyl, trifluoromethyl, trifluoromethoxy, hydroxy, benzyloxy, carboxy, carboalkoxy of 2 to 4 carbon atoms, acyloxy of 1 to 10 carbon atoms, dialkylamino where alkyl has from 1 to 4 carbon atoms, and dialkylaminoalkoxy where alkyl has from 1 to 4 carbon atoms and alkoxy has from 2 to 4 carbon atoms.

Also within the scope of the invention are pharmaceutically acceptable heavy metal chelates of the foregoing compounds, wherein the metal is complexed with the carbonyl groups of the diketone or keto-ester moiety. Such metals include copper (valence II), nickel, cobalt and the like.

In the above general formula I, Alk stands for a saturated aliphatic hydrocarbon bridge containing from 3 to 10 carbon atoms. The alkylene bridge may be straight or branched. A preferred class of compounds are those where Alk is straight chain alkylene of 3 to 10 carbon atoms, and if the Alk bridge is branched, it is preferred that it be symmetrical, that is with the branching at the same relative positions from either end of the bridge.

The alkylene bridge, Alk, is optionally interrupted by an oxygen atom separated by at least two carbon atoms from the terminal bonds of Alk. The oxygen atom is preferably in the center of the alkylene bridge, equidistant from the terminal bonds of Alk.

The carbon chains of R and R' can be straight or branched.

When two or three monovalent substituents are present on the phenyl ring of Ar, they can be the same or different. In the event alkoxyalkoxy is present on the phenyl ring, it is preferred that the two oxygen atoms therein be separated by at least two carbon atoms. It is also preferred that no more than one nitro or sulfo group be present on the phenyl ring.

The compounds of the invention are prepared according to the following reaction sequence:

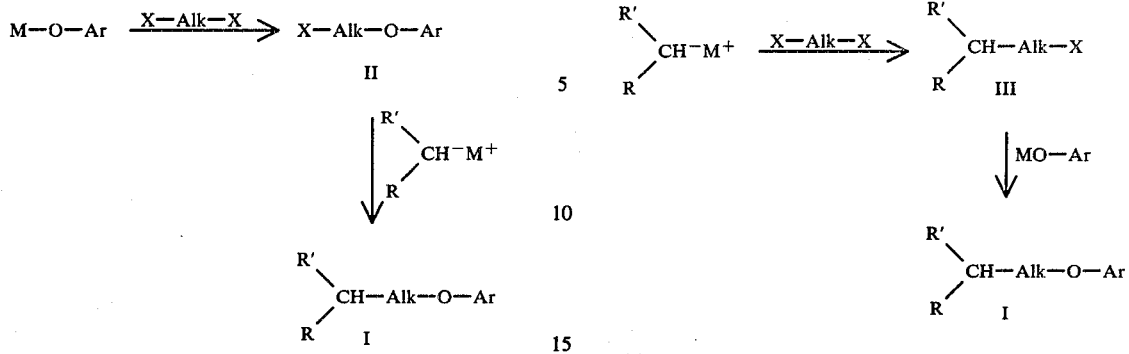

An alkali metal salt of a phenol (HOAr), M-O-Ar, where M is alkali metal, preferably sodium or potassium, is interacted with an alkylene dihalide, X—Alk—X, where X is chlorine, bromine or iodine. The reaction takes place with moderate heating, between about 50° and 100° C. in an inert solvent using equimolar quantities of reactants, or preferably a stoichiometric excess of dihalide to minimize di-ether (Ar—O—Alk—O—Ar) formation. The di-ether that is formed is readily separated from the desired mono-ether (II), because the former is a relatively high melting solid which separates readily from organic solvents while the mono-ether remains in solution.

In the final step, the mono-ether, X—Alk—O—Ar (II), is treated with the alkali metal enolate salt of a diketone or keto-ester of formula RR'CH$^-$M$^+$, where R and R' have the meanings given hereinabove and M$^+$ is an alkali metal cation, preferably lithium, sodium or potassium. The reaction takes place in an inert solvent under anhydrous conditions at ambient temperature or slightly above (25°–70° C.). If the mono-ether, X—Alk—O—Ar, is a chloride (X = Cl), it is preferably converted to the more reactive iodide (X = I) with an alkali metal iodide, prior to the final alkylation step.

If it is desired to obtain compounds of formula I wherein Ar is substituted by one to three hydroxy groups, the reaction between M-OAr and X—Alk—X can be carried out with the corresponding compounds where Ar is substituted by one to three benzyloxy or acyloxy groups. The benzyloxy or acyloxy group or groups can then be cleaved by catalytic hydrogenolysis or hydrolysis, respectively.

It is not, however, essential that phenolic hydroxy groups be protected in the form of ethers or esters at the final stage of the synthesis because the diketone or keto-ester reactant, RR'CH$_2$, is more acidic than the phenolic hydroxyl; hence the desired alkylation with the iodides or bromides (II, X is I or Br) will take place without affecting any phenolic hydroxy groups which may be present.

Alternatively, in the final step, the alkali metal enolate salt can be replaced by a heavy metal chelate of the diketone or keto-ester. Appropriate heavy metal chelates include the copper, nickel or cobalt chelates.

An alternative approach to the compounds of the invention is depicted in the following reaction sequence:

In this alternative approach an alkali metal enolate salt or a heavy metal chelate of a diketone or keto-ester (RR'CH$_2$) is interacted with an alkylene dihalide, X—Alk—X. The reaction takes place in an inert solvent under anhydrous conditions at ambient temperature or slightly above (20°–70° C.), using equimolar quantities of reactants or a stoichiometric excess of dihalide. The resulting haloalkyl diketone or keto-ester of formula III is then interacted with an alkali metal salt of a phenol (HOAr), which reaction takes place with moderate heating, between about 50° and 100° C. in an inert solvent under anhydrous conditions. In this approach, any free hydroxy groups present in Ar should be protected in the form of the benzyl ether or an ester in order to prevent competing reactions with the haloalkyl diketone.

The intermediates of formula III are novel compounds and within the purview of the invention.

It is preferred to carry out the initial etherification step with a dibromide (X—Alk—X where X is Br) because of the more ready availability of dibromides as compared to diiodides. The resulting bromide (X—Alk-—O—Ar or RR'CH—Alk—X where X is Br) can be interacted directly with the alkali metal enolate salt RR'CH$^-$M$^+$ or phenolate ArO$^-$M$^+$, respectively; or if desired converted to the corresponding iodide (X—Alk—O—Ar or RR'CH—Alk—X where X is I) which reacts somewhat more easily with the enolate or phenolate salt than does the bromide. The conversion of II (X = Br) to II (X = I) or III (X = Br) to III (X = I) is effected by heating the former with sodium or potassium iodide in an inert solvent, e.g. acetone.

The dihalides, X—Alk—X, where Alk is branched or oxygen interrupted are preferably symmetrical, that is, the branching or hetero atom is in the same relative position or positions with respect to the terminal halogen atoms, in order to avoid production of mixtures upon ether formation.

It is also possible to employ chlorobromoalkanes as the dihalide reactant, namely, Cl—Alk—Br. The use of such mixed dihalides has the advantage that di-ether formation is eliminated or minimized, since reaction occurs preferentially with the bromine atom, especially if stoichiometric proportions of phenol and dihalide are used. Furthermore, it is possible by this variation in the procedure to obtain compounds with unsymmetrically branched or oxygen interrupted alkylene bridges without producing mixtures. The resulting chloroalkoxy aryl ether, Cl—Alk—O—Ar, or chloroalkyl diketone or keto-ester, Cl—Alk—CHR'R, must then be converted to the corresponding bromo or iodo compound before it will react with the alkali metal phenolate or the alkali metal enolate salt of a diketone or keto-ester, respectively. The chlorobromoalkane starting materials can be prepared by reduction, e.g. with lithium aluminum hydride, of a chloro-ester, Cl—Alk'—COOCH$_3$, to afford a chloroalkanol, Cl—Alk—OH, followed by replacement of the hydroxy group with bromine, e.g. with phosphorus tribromide.

It is preferred to prepare compounds of formula I where the aryl group is substituted by acyloxy by esterification of the corresponding hydroxy compounds with the appropriate acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formyl, acetyl, propionyl, butyryl, isobutyryl, caproyl, heptanoyl, octanoyl, trimethylacetyl, and the like; carboxy-lower-alkanoyl radicals, e.g., succinyl ($\beta$-carboxypropionyl); cycloalkyl-lower-alkanoyl radicals, e.g., $\beta$-cyclopentylpropionyl, $\beta$-cyclohexylpropionyl, and the like; monocarbocyclic aroyl radicals, e.g., benzoyl, p-toluyl, p-nitrobenzoyl, 3,4,5-trimethoxybenzoyl, and the like; monocarbocyclic aryl-lower-alkanoyl or -alkenoyl radicals, such as phenylacetyl, $\beta$-phenylpropionyl, cinnamoyl, and the like; and monocarbocyclic aryloxy-lower-alkanoyl radicals, such as p-chlorophenoxyacetyl, and the like; and amino-lower-alkanoyl, such as glycinyl, alaninyl, diethylaminopropionyl, piperidinopropionyl, pyrrolidinopropionyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups, which substituents, if plural, can be the same or different. It is preferred that no more than one nitro group be present.

It is preferred to prepare compounds of formula I where the aryl group is substituted by carboxyl (COOH) by hydrolysis of the corresponding compounds of formula I where the aryl group is substituted by carboalkoxy. A sulfo group can be introduced into the aryl group of a compound of formula I by direct sulfonation with sulfuric acid.

It is preferred to prepare compounds of formula I where the aryl group is substituted by dialkylaminoalkoxy by etherification of the corresponding compounds of formula I where the aryl group is substituted by hydroxy, effected by reacting an alkali metal salt of the latter with a dialkylaminoalkyl halide.

Biological evaluation of the compounds of the invention has shown that they possess antiviral activity. They have been found to be effective against one or more of a large variety of RNA and DNA viruses, including Myxoviruses, e.g. influenza types A$_0$, A$_1$, A-2, B; Paramyxoviruses, e.g. parainfluenza types 1, 2, 3, and mumps virus; Picornaviruses, e.g. human rhinoviruses, Coxsackie viruses types A, B, ECHO viruses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpesvirus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures.

The structures of the compounds of the invention are established by the modes of synthesis, by elementary analysis, and by infrared and nuclear magnetic resonance spectral determinations.

A still further aspect of the invention relates to compositions for combatting viruses which comprise an anti-virally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

EXAMPLE 1

(a) 7-(4-Carbethoxyphenoxy)heptyl bromide

A mixture of 24 g. (0.144 mole) of ethyl p-hydroxybenzoate, 66 g. (0.256 mole) of 1,7-dibromoheptane, 38.6 g. (0.28 mole) of powdered potassium carbonate and 250 ml. of acetone was heated at reflux for 22 hours. The reaction mixture was concentrated in vacuo and the residue partitioned between water and methylene dichloride. The organic layer was washed with sodium chloride solution and water, dried and concentrated. The residue was distilled to give 33.8 g. of 7-(4-carbethoxyphenoxy)heptyl bromide, b.p. 155°-170° C. (0.01 mm.).

By replacing the 1,7-dibromoheptane by a molar equivalent amount of 1,3-dibromopropane there can be obtained 7-(4-carbethoxyphenoxy)propyl bromide.

(b) 7-(4-Carbethoxyphenoxy)heptyl iodide

A mixture of 33.8 g. (0.0985 mole) of 7-(4-carbethoxyphenoxy)heptyl bromide, 15.6 g. (0.104 mole) of sodium iodide and 350 ml. of acetone was heated at reflux for two hours. The reaction mixture was cooled, filtered and concentrated in vacuo. The residue was partitioned between water and ether, and the ether layer was washed with water, dried and concentrated, to give 38 g. of 7-(4-carbethoxyphenoxy)heptyl iodide, used directly in the following reaction.

Similarly, 7-(4-carbethoxyphenoxy)propyl bromide can be converted to 7-(4-carbethoxyphenoxy)propyl iodide.

(c) 4-[7-(4-Carbethoxyphenoxy)heptyl]-3,5-heptanedione [I; Ar is 4-C$_2$H$_5$OCOC$_6$H$_4$, Alk is (CH$_2$)$_7$, R and R' are CH$_3$CH$_2$CO]

The lithium salt of 3,5-heptanedione was prepared from 91.2 g. (0.72 mole) of 3,5-heptanedione and 0.676 mole of butyllithium (1.6 molar in ether, 425 ml.) and 1200 ml. of ether, stirred for one hour. The lithium salt separated from solution and was collected by filtration (81 g.). Nineteen grams (0.142 mole) of the lithium salt was added to a solution of 38 g. (0.0975 mole) of 7-(4-carbethoxyphenoxy)heptyl iodide in 300 ml. of dimethylformamide, and the reaction mixture was stirred for 15 hours at 60°-70° C. The reaction mixture was concentrated in vacuo and the residue partitioned between water and ether. The ether layer was washed with water, sodium chloride solution and again with water, dried over anhydrous magnesium sulfate and concentrated. The residue was distilled to give 4-[7-(4-carbethoxyphenoxy)-heptyl]-3,5-heptanedione as a yellow oil, b.p. 172°-202° C. (0.008 mm.).

Anal. Calcd. for $C_{23}H_{34}O_5$: C, 70.74; H, 8.78. Found: C, 70.76; H, 8.77.

IR (oil film) $\lambda_\mu^{max}$ 3.42mss + shldrs. (CH); 5.85s + shldrs. (C=O); 6.24s, 6.34m, 6.61m, 6.83m + shldrs. (arom. and CH).

By replacing the 3,5-heptanedione in the foregoing preparation by a molar equivalent amount of 2,4-pentanedione or 4,6-nonanedione there can be obtained, respectively, 3-[7-(4-carbethoxyphenoxy)heptyl]-2,4-pentanedione [I; Ar is 4-$C_2H_5OCOC_6H_4$, Alk is $(CH_2)_7$, R and R' are $CH_3CO$], or 5-[7-(4-carbethoxyphenoxy)-heptyl]-4,6-nonanedione [I; Ar is 4-$C_2H_5OCOC_6H_4$, Alk is $(CH_2)_7$, R and R' are $CH_3CH_2CH_2CO$].

By replacing the 7-(4-carbethoxyphenoxy)heptyl iodide in the foregoing preparation by a molar equivalent amount of 3-(4-carbethoxyphenoxy)propyl iodide, there can be obtained 4-[3-(4-carbethoxyphenoxy)propyl]-3,5-heptanedione [I; Ar is 4-$C_2H_5OCOC_6H_4$, Alk is $(CH_2)_3$, R and R' are $CH_3CH_2CO$].

EXAMPLE 2

4-[7-(4-Carboxyphenoxy)heptyl]-3,5-heptanedione [I; Ar is 4-$HOOCC_6H_4$, Alk is $(CH_2)_7$, R and R' are $CH_3CH_2CO$]

A solution of 10.7 g. of 4-[7-(4-carbethoxyphenoxy)-heptyl]-3,5-heptanedione (Example 1) and 3 ml. of concentrated hydrochloric acid in 150 ml. of dioxane was heated at reflux for 48 hours. The solution was treated with activated charcoal, filtered and evaporated to dryness. The residue was taken up in ether and extracted with 10% potassium carbonate solution. The basic extracts were acidified and the acidified mixture extracted with ether. The ether solution was dried and evaporated, and the residue crystallized from ether to give 5.5 g. of 4-[7-(4-carboxyphenoxy)heptyl]-3,5-heptanedione, m.p. 105°-107° C.

Anal. Calcd. for $C_{21}H_{30}O_5$: C, 69.59; H, 8.34. Found: C, 69.50; H, 8.32.

IR (½% KBr) $\lambda_\mu^{max}$ 3.42mss + shldrs., 3.52ms (CH); 3.70-4.0m, fine structure (chelate H-bonding); 5.85s, 5.98s + shldrs. (C=O); 6.24s, 6.34m, 6.61m, 6.81m, 6.98 + shldrs. (arom. and CH).

EXAMPLE 3

(a) 4-(6-Bromohexyl)-3,5-heptanedione

A solution of 64.1 g. of 3,5-heptanedione in 200 ml. of dimethylformamide was added over a period of one hour to a suspension of 3.65 g. of lithium hydride in 400 ml. of dimethylformamide. The mixture was stirred for one hour and 488 g. of 1,6-dibromohexane was then added all at once. The reaction mixture was warmed at 60°-70° C. for 24 hours. The volatile solvent was removed and the residue partitioned between water and methylene dichloride. The methylene dichloride solution was concentrated and the residue distilled to give 65.0 g. of 4-(6-bromohexyl)-3,5-heptanedione, b.p. 118°-124° C. (0.005 mm.).

By substituting for the 1,6-dibromohexane the corresponding homologous dibromoalkanes, there were prepared 4-(8-bromooctyl)-3,5-heptanedione, b.p. 136°-139° C. (0.004 mm.); 4-(9-bromononyl)-3,5-heptanedione, b.p. 135°-137° C. (0.004 mm.); and 4-(10-bromodecyl)-3,5-heptanedione, b.p. 157°-159° C. (0.005 mm.).

By selecting the appropriate alkane dibromide and dione, there can be prepared 3-(3-bromopropyl)-2,4-pentanedione, 4-(6-bromohexyl)-2,2,6,6-tetramethyl-3,5-pentanedione, 5-(6-bromohexyl)-4,6-nonanedione, and the like.

(b)

4-[10-(4-Carbethoxyphenoxy)decyl]-3,5-heptanedione [I; Ar is $C_2H_5OCOC_6H_4$, Alk is $(CH_2)_{10}$, R and R' are $CH_3CH_2CO$]

A mixture of 26.3 g. (0.0758 mole) of 4-(6-bromohexyl)-3,5-heptanedione, 13.1 g. (0.0787 mole) of ethyl p-hydroxybenzoate, 31.5 g. (0.228 mole) of powdered potassium carbonate, 4 g. of potassium iodide and 500 ml. of acetone was heated at reflux for 36 hours. The reaction mixture was concentrated in vacuo and partitioned between water and methylene dichloride. The organic layer was washed successively with sodium hydroxide solution, water, hydrochloric acid, water and sodium chloride solution, and then dried over anhydrous magnesium sulfate. The solution was concentrated and the residue crystallized and recrystallized from n-pentane to give 4-[10-(4-carbethoxyphenoxy)-decyl]-3,5-heptanedione, m.p. 45°-46° C.

Anal. Calcd. for $C_{26}H_{40}O_5$: C, 72.19; H, 9.32. Found: C, 72.69; H, 9.15.

According to the procedures described above in Examples 1, 2 and 3, selecting the appropriate substitute phenol, alkylene dibromide and diketone, the following compounds were prepared:

EXAMPLE 4

4-[8-(4-Carbethoxyphenoxy)octyl]-3,5-heptanedione [I; Ar is 4-$C_2H_5OCOC_6H_4$, Alk is $(CH_2)_8$, R and R' are $CH_3CH_2CO$], b.p. 219°-221° C. (0.008 mm.).

Anal. Calcd. for $C_{24}H_{36}O_5$: C, 71.26; H, 8.97. Found: C, 70.88; H, 8.94.

EXAMPLE 5

4-[9-(4-Carbethoxyphenoxy)nonyl]-3,5-heptanedione [I; Ar is 4-$C_2H_5OCOC_6H_4$, Alk is $(CH_2)_9$, R and R' are $CH_3CH_2CO$], m.p. 65°-66° C.

Anal. Calcd. for $C_{25}H_{38}O_5$: C, 71.74; H, 9.15. Found: C, 72.10; H, 9.30.

EXAMPLE 6

4-[9-(4-Carbomethoxyphenoxy)nonyl]-3,5-heptanedione [I; Ar is 4-$CH_3OCOC_6H_4$, Alk is $(CH_2)_9$, R and R' are $CH_3CH_2CO$], colorless needles, m.p. 76°-77° C.

Anal. Calcd. for $C_{24}H_{36}O_5$: C, 71.26; H, 8.97. Found: C, 71.53; H, 9.06.

EXAMPLE 7

4-[8-(4-Carboxyphenoxy)octyl]-3,5-heptanedione [I; Ar is 4-HOOCC$_6$H$_4$, Alk is (CH$_2$)$_8$, R and R' are CH$_3$CH$_2$CO], m.p. 102°–104° C.

Anal. Calcd. for C$_{22}$H$_{32}$O$_5$: C, 70.19; H, 8.57. Found: C, 70.66; H, 8.58.

EXAMPLE 8

4-[6-(4-Carbethoxyphenoxy)hexyl]-3,5-heptanedione [I; Ar is 4-C$_2$H$_5$OCOC$_6$H$_4$, Alk is (CH$_2$)$_6$, R and R' are CH$_3$CH$_2$CO], m.p. 47°–48° C.

Anal. Calcd. for C$_{22}$H$_{32}$O$_5$: C, 70.19; H, 8.57. Found: C, 70.33; H, 8.70.

EXAMPLE 9

4-[6-(4-Carboxyphenoxy)hexyl]-3,5-heptanedione [I; Ar is 4-HOOCC$_6$H$_4$, Alk is (CH$_2$)$_6$, R and R' are CH$_3$CH$_2$CO], m.p. 99°–101° C.

Anal. Calcd. for C$_{20}$H$_{28}$O$_5$: C, 68.94; H, 8.10. Found: C, 69.32; H, 8.36.

EXAMPLE 10

4-[10-(4-Carbomethoxyphenoxy)decyl]-3,5-heptanedione [I; Ar is 4-CH$_3$OCOC$_6$H$_4$, Alk is (CH$_2$)$_{10}$, R and R' are CH$_3$CH$_2$CO], colorless solid, m.p. 71°–72° C.

Anal. Calcd. for C$_{25}$H$_{38}$O$_5$: C, 71.74; H, 9.15. Found: C, 72.04; H, 9.19.

EXAMPLE 11

4-[6-(2-Chloro-4-carbomethoxyphenoxy)hexyl]-3,5-heptanedione [I; Ar is 2-Cl-4-CH$_3$OCOC$_6$H$_3$, Alk is (CH$_2$)$_6$, R and R' are CH$_3$CH$_2$CO], b.p. 205°–210° C. (0.03 mm.).

Anal. Calcd. for C$_{21}$H$_{29}$ClO$_5$: C, 63.54; H, 7.36; Cl, 8.93. Found: C, 63.53; H, 7.31; Cl, 8.92.

EXAMPLE 12

4-[6-(2-Chloro-4-carboxyphenoxy)hexyl]-3,5-heptanedione [I; Ar is 2-Cl-4-HOOCC$_6$H$_3$, Alk is (CH$_2$)$_6$, R and R' are CH$_3$CH$_2$CO], m.p. 108°–109° C.

Anal. Calcd. for C$_{20}$H$_{27}$ClO$_5$: C, 62.74; H, 7.10; Cl, 9.25. Found: C, 62.61; H, 7.11; Cl, 9.37.

EXAMPLE 13

4-[6-(2-Bromo-4-carbomethoxyphenoxy)hexyl]-3,5-heptanedione [I; Ar is 2-Br-4-CH$_3$OCOC$_6$H$_3$, Alk is (CH$_2$)$_6$, R and R' are CH$_3$CH$_2$CO], light yellow oil.

Anal. Calcd. for C$_{21}$H$_{29}$BrO$_5$: C, 57.14; H, 6.62; Br, 18.10. Found: C, 57.37; H, 6.64; Br, 18.17.

We claim:
1. A compound of the formula

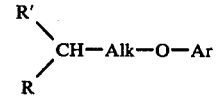

wherein:
Alk is alkylene of 3 to 10 carbon atoms;
R and R' are alkanoyl of 2 to 6 carbon atoms;
and Ar is phenyl substituted by a member of the group consisting of carboxy and carboalkoxy of 2 to 4 carbon atoms, optionally further substituted by a halogen atom.

2. 4-[7-(4-Carbethoxyphenoxy)heptyl]-3,5-heptanedione, according to claim 1.
3. 4-[7-(4-Carboxyphenoxy)heptyl]-3,5-heptanedione, according to claim 1.
4. 4-[10-(4-Carbethoxyphenoxy)decyl]-3,5-heptanedione, according to claim 1.
5. 4-[8-(4-Carbethoxyphenoxy)octyl]-3,5-heptanedione, according to claim 1.
6. 4-[9-(4-Carbethoxyphenoxy)nonyl]-3,5-heptanedione, according to claim 1.
7. 4-[9-(4-Carbomethoxyphenoxy)nonyl]-3,5-heptanedione, according to claim 1.
8. 4-[8-(4-Carboxyphenoxy)octyl]-3,5-heptanedione, according to claim 1.
9. 4-[6-(4-Carbethoxyphenoxy)hexyl]-3,5-heptanedione, according to claim 1.
10. 4-[6-(4-Carboxyphenoxy)hexyl]-3,5-heptanedione, according to claim 1.
11. 4-[10-(4-Carbomethoxyphenoxy)decyl]-3,5-heptanedione, according to claim 1.
12. 4-[6-(2-Chloro-4-carbomethoxyphenoxy)hexyl]-3,5-heptanedione, according to claim 1.
13. 4-[6-(2-Chloro-4-carboxyphenoxy)hexyl]-3,5-heptanedione, according to claim 1.
14. 4-[6-(2-Bromo-4-carbomethoxyphenoxy)hexyl]-3,5-heptanedione, according to claim 1.
15. A composition for combatting viruses which comprises an antivirally effective amount of at least one compound according to claim 1 in admixture with a suitable carrier or diluent.
16. A method for combatting viruses which comprises contacting the locus of said viruses with a composition containing an antivirally effective amount of at least one compound according to claim 1 in admixture with a suitable carrier or diluent.

* * * * *